US010390986B2

(12) United States Patent
Feris et al.

(10) Patent No.: US 10,390,986 B2
(45) Date of Patent: Aug. 27, 2019

(54) CONTROL DEVICE FOR CONTROLLING A RIGIDITY OF AN ORTHOSIS AND METHOD OF CONTROLLING A RIGIDITY OF AN ORTHOSIS (71) Applicant: International Business Machines Corporation, Armonk, NY (US)

(72) Inventors: Rogerio Schmidt Feris, Hartford, CT (US); Minkyong Kim, Scarsdale, NY (US); Clifford A. Pickover, Yorktown Heights, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 348 days.

(21) Appl. No.: 14/954,905

(22) Filed: Nov. 30, 2015

(65) Prior Publication Data

US 2017/0151081 A1    Jun. 1, 2017

(51) Int. Cl.
*A61B 5/00* (2006.01)
*A61B 5/11* (2006.01)
*A61F 2/68* (2006.01)
*A61F 5/01* (2006.01)

(52) U.S. Cl.
CPC .......... *A61F 5/0102* (2013.01); *A61B 5/1117* (2013.01); *A61B 5/4851* (2013.01); *A61B 5/6812* (2013.01); *A61B 5/7264* (2013.01); *A61F 2/68* (2013.01); *A61F 5/0123* (2013.01); *A61F 2005/016* (2013.01); *A61F 2005/0155* (2013.01); *A61F 2005/0167* (2013.01); *A61F 2005/0181* (2013.01)

(58) Field of Classification Search
None
See application file for complete search history.

(56) References Cited

U.S. PATENT DOCUMENTS

| 6,113,642 | A | * | 9/2000 | Petrofsky | ................. A61F 2/68 188/282.3 |
|---|---|---|---|---|---|
| 7,578,799 | B2 | | 8/2009 | Thorsteinsson et al. | |
| 7,921,973 | B2 | | 4/2011 | Wereley et al. | |
| 8,138,882 | B2 | | 3/2012 | Do et al. | |
| 8,142,370 | B2 | | 3/2012 | Weinberg et al. | |
| 8,179,268 | B2 | | 5/2012 | Gannot et al. | |

(Continued)

FOREIGN PATENT DOCUMENTS

| CN | 101450016 A | 6/2009 |
|---|---|---|
| CN | 102722721 A | 10/2012 |

(Continued)

OTHER PUBLICATIONS

SmartCells Fall Protection Data & Research, http://www.smartcellsusa.com.

(Continued)

*Primary Examiner* — Shaun M Campbell
(74) *Attorney, Agent, or Firm* — Rahan Uddin, Esq.; McGinn IP Law Group, PLLC (57) ABSTRACT A control device for controlling a rigidity of an orthosis, includes a sensing circuit for sensing a falling motion, a signal generating circuit which generates a sensing signal based on the sensing of the falling motion, and a rigidity control mechanism which controls a rigidity of the orthosis based on the sensing signal.

18 Claims, 10 Drawing Sheets (56) References Cited

U.S. PATENT DOCUMENTS

| | | | | |
|---|---|---|---|---|
| 2002/0183673 A1* | 12/2002 | Naft | ...................... | A61F 5/0125 |
| | | | | 602/16 |
| 2003/0212356 A1* | 11/2003 | Scorvo | .................. | A61F 5/0125 |
| | | | | 602/20 |
| 2006/0248750 A1 | 11/2006 | Rossenberg | | |
| 2010/0116277 A1* | 5/2010 | Lanfermann | ........ | A61B 5/1038 |
| | | | | 128/846 |
| 2011/0082672 A1* | 4/2011 | Hardigan | ................ | G06F 19/00 |
| | | | | 703/2 |
| 2012/0238914 A1* | 9/2012 | Goldfield | ............. | A61B 5/6804 |
| | | | | 600/595 |
| 2014/0276130 A1* | 9/2014 | Mirelman | .............. | A61B 5/744 |
| | | | | 600/483 |
| 2015/0018733 A1* | 1/2015 | Ben-Meir | ............. | A61F 5/0104 |
| | | | | 602/6 |
| 2015/0245927 A1 | 9/2015 | Thorsteinsson et al. | | |
| 2016/0220153 A1* | 8/2016 | Annegarn | ............. | A61B 5/1117 |

FOREIGN PATENT DOCUMENTS

| | | |
|---|---|---|
| CN | 103417219 A | 12/2013 |
| CN | 103731557 A | 4/2014 |
| EP | 2 575 113 A1 | 4/2013 |
| WO | WO 2013/033669 A2 | 3/2013 |

OTHER PUBLICATIONS

Electrorheological Fluid Phones, http://www.unwired.com/2008/01/25/foldable-rollable-phone-from-motorola/.

* cited by examiner

CONTROL DEVICE FOR CONTROLLING A RIGIDITY OF AN ORTHOSIS AND METHOD OF CONTROLLING A RIGIDITY OF AN ORTHOSIS

BACKGROUND OF THE INVENTION

Field of the Invention

The present invention relates to a control device for controlling a rigidity of an orthosis, and a method of controlling a rigidity of an orthosis, and in particular, a control device which includes a sensing circuit for sensing a falling motion.

Description of the Related Art

An orthosis is a device such as a cast, brace or splint that may be used to stabilize, reinforce or immobilize a body part such as the spine or hip, or an extremity such as a leg, foot, arm, or finger.

Such devices serve many functions in many different fields. For example, an orthosis may be used in the medical field to allow bone healing, or provide a mechanical block to prevent undesired movement, and in the rehabilitative field to functionally assist weak muscles, or protect a limb with pressure sores.

Figure 1A:
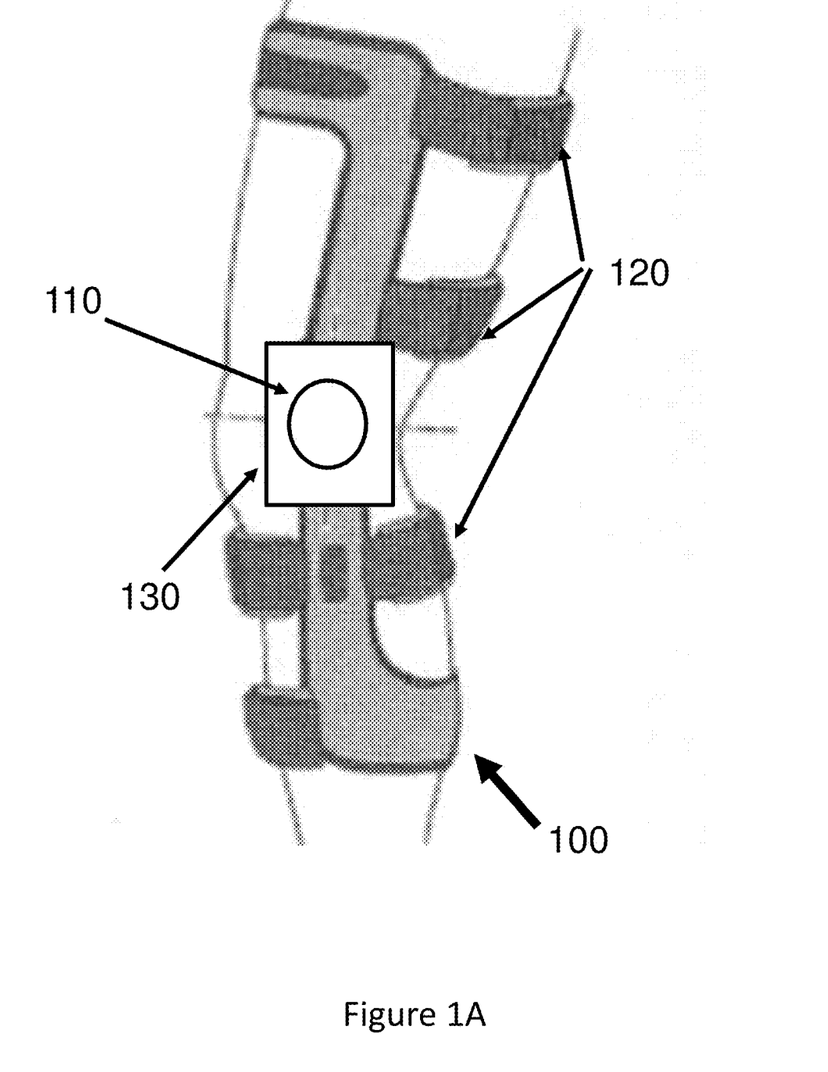
FIG. 1A illustrates a conventional orthosis 100 (e.g., knee brace), which includes an brake/actuator device 110 (e.g., electro-rheological fluid (ERF) Brake), and a plurality of straps 120 for holding the orthosis 100 onto a limb (e.g., a leg)

FIG. 1A illustrates a conventional orthosis 100 (e.g., hinged knee brace) which includes an brake/actuator device 110 (e.g., electro-rheological fluid (ERF) Brake), and a plurality of straps 120 for holding the orthosis 100 onto a limb (e.g., a leg). The conventional orthosis 100 also includes a hinge 130 on which the brake/actuator device 110 is mounted. The orthosis 100 may be solely a resistive element or may also provide torque generation depending on the desired application.

Figure 1B:
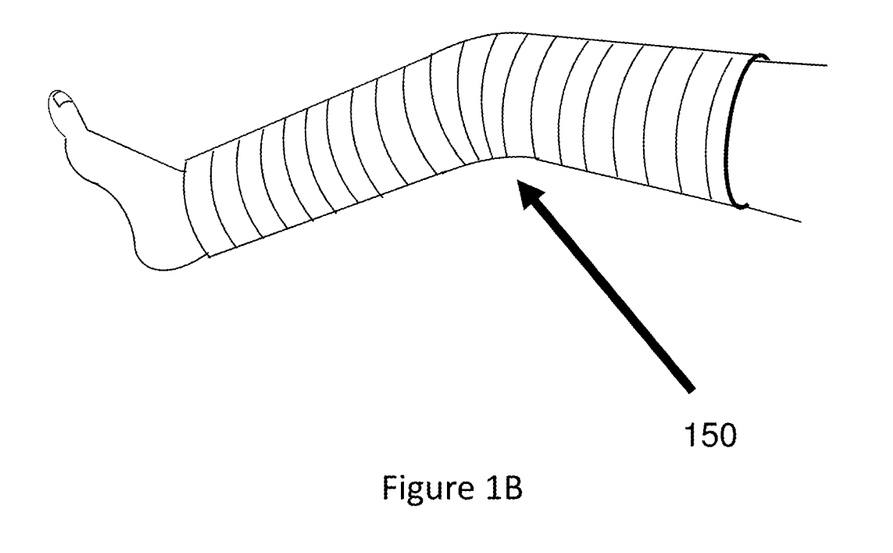
FIG. 1B illustrates another conventional orthosis 150 (e.g., a cast)

FIG. 1B illustrates another conventional orthosis 150 which is commonly referred to as a "cast", and may be used to immobilize an injured body part. The orthosis 150 may be rigid or semi-rigid in order to restrict movement of the injured body part.

SUMMARY OF THE INVENTION

In view of the foregoing and other problems, disadvantages, and drawbacks of the aforementioned conventional systems and methods, an exemplary aspect of the present invention is directed to an orthosis (and method of controlling a rigidity of an orthosis), which are more effective and more efficient than conventional orthoses.

An exemplary aspect of the present invention is directed to a control device for controlling a rigidity of an orthosis, including a sensing circuit for sensing a falling motion, a signal generating circuit which generates a sensing signal based on the sensing of the falling motion, and a rigidity control mechanism which controls a rigidity of the orthosis based on the sensing signal.

Another exemplary aspect of the present invention is directed to a method of controlling a rigidity of an orthosis, the method including sensing a falling motion, generating a sensing signal based on the sensing of the falling motion, and controlling a rigidity of the orthosis based on the sensing signal.

Another exemplary aspect of the present invention is directed to a programmable storage medium tangibly embodying a program of machine-readable instructions executable by a digital processing apparatus to perform a method of controlling a rigidity of an orthosis, the method including sensing a falling motion, generating a sensing signal based on the sensing of the falling motion, and controlling a rigidity of the orthosis based on the sensing signal.

With its unique and novel features, the present invention provides a control device for controlling a rigidity of an orthosis (and method of controlling a rigidity of an orthosis), which are more effective and more efficient than conventional devices.

BRIEF DESCRIPTION OF THE DRAWINGS

The foregoing and other objects, aspects and advantages will be better understood from the following detailed description of the embodiments of the invention with reference to the drawings, in which.

DETAILED DESCRIPTION OF THE EXEMPLARY EMBODIMENTS OF THE INVENTION

Referring now to the drawings, FIGS. 2-9 illustrates the exemplary aspects of the present invention.

In the event that a subject who is wearing an orthosis would fall, if the rigidity of the orthosis is low, the orthosis may not be sufficient to prevent an injury to the subject. For example, if the subject is wearing the conventional orthosis 100 on his leg to protect a surgically-repaired knee, and the subject falls, the rigidity of the hinge 130 may not be sufficient to prevent further injury to the subject's surgically-repaired knee.

Thus, a problem of the conventional orthosis 100 is that is does not sense a falling motion, and control a rigidity of the orthosis 100 based on a sensing signal. Another problem of the conventional orthosis 100 is that is does not consider a cognitive state of the subject, or a location (e.g., high risk area such as stairs) of the orthosis 100 in setting a rigidity of the orthosis 100 (e.g., a rigidity of the hinge 130).

The exemplary aspects of the present invention may address the problems of the conventional orthosis 100.

Figure 2:
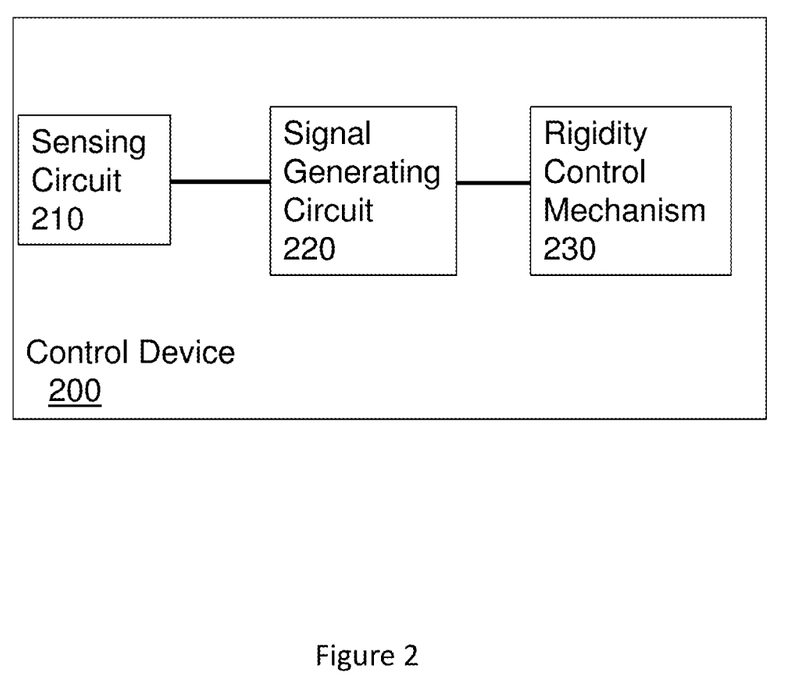
FIG. 2 illustrates a control device 200 for controlling a rigidity of an orthosis (e.g., cast, brace, splint, elbow hinge, etc.) according to an exemplary aspect of the present invention.

FIG. 2 illustrates a control device 200 for controlling a rigidity of an orthosis (e.g., cast, brace, splint, elbow hinge, etc.) according to an exemplary aspect of the present invention.

The control device 200 may be utilized, for example, in an intelligent orthoses that can change rigidity (e.g., stiffness) coupled with a fall detection capability (e.g., sensing a falling motion), and a fall likelihood determination capability (i.e., fall inferring/predicting and preemption capability).

As illustrated in FIG. 2, the control device 200 includes a sensing circuit 210 for sensing a falling motion, a signal generating circuit 220 which generates a sensing signal based on the sensing of the falling motion, and a rigidity control mechanism 230 which controls a rigidity of the orthosis based on the sensing signal.

It should be noted that term "falling" as used herein, should be construed to include, for example, slipping, tripping, stumbling, moving downward, dropping and descending. It should also be noted that the term "subject" as used herein, should be construed to mean a human subject, or other animal subject (e.g., a horse, dog, cat, etc.), or a mechanical subject (e.g., a robot).

The control device 200 may use the sensing circuit 210 to sense that the subject wearing the orthosis 200 is falling. The sensing circuit 210 may include, for example, an accelerometer, a video capture device, a passive infrared (PR) detection unit having a given field of view, a machine vision/depth camera, a smartphone-based real-time falling detection system. The sensing circuit 210 may also include a wearable human body falling detection device which is composed of embedded type multi-sensor hardware.

In particular, the sensing circuit 210 may detect a fall (e.g., sense a falling motion) by monitoring the subject's body posture and detecting a change in the subject's body posture by embedded multi-sensor hardware through an acceleration sensor and a tilt angle sensor which may be formed, for example, on the orthosis which is worn by the subject.

Further, the control device 200 may, based on the sensing, transmit a sensing signal, and control a rigidity of the orthosis 200 with a rigidity control mechanism which may include, for example, an electrorheological (ER fluid) or magnetorheological fluid (MR fluid) that changes viscosity in response to the sensing signal.

An electrorheological (ER) fluids is a suspension of extremely fine non-conducting particles (up to 50 micrometers in diameter) in an electrically insulating fluid. The apparent viscosity of these fluids changes reversibly by an order of up to 100,000 in response to an electric field. For example, a typical ER fluid can go from the consistency of a liquid to that of a gel, and back, with response times on the order of milliseconds.

A magnetorheological fluid (MR fluid) is a type of smart fluid in a carrier fluid, usually a type of oil. When subjected to a magnetic field, the fluid greatly increases its apparent viscosity, to the point of becoming a viscoelastic solid.

The MR fluid may be used, for example, in a magnetorheological damper. Magnetorheological damper are commonly utilized in semi-active human prosthetic legs. Much like those used in military and commercial helicopters, a damper in the prosthetic leg decreases the shock delivered to the patient's leg when jumping, for example. This results in an increased mobility and agility for the patient." An exemplary aspect of the present invention may use the MR fluid as the main material for the orthosis to better control the rigidity (e.g., stiffness) of the orthosis and also to dampen the shock in case of a fall or other undesirable movement by the subject wearing the orthosis.

The control device 200 may also store information pertaining to a cognitive state of the subject (e.g., drowsiness, drunk, etc.) along with other conditions (e.g., mental health of the subject, such as whether the subject has Alzheimer's or Parkinson's disease, etc.), and control the rigidity of an orthosis based on this information.

Thus, for example, the control device 200 may identify the subject wearing the orthosis as a person of "high fall risk", or "low fall risk", etc. based on the subject's cognitive state. Such cognitive states, which would place a person at risk of falling, include, for example, nausea, drowsiness, an inebriated condition, but also extreme stress level. The control device 200 may utilize one or more methods for identifying the cognitive state of the subject wearing the orthosis.

Figure 3:
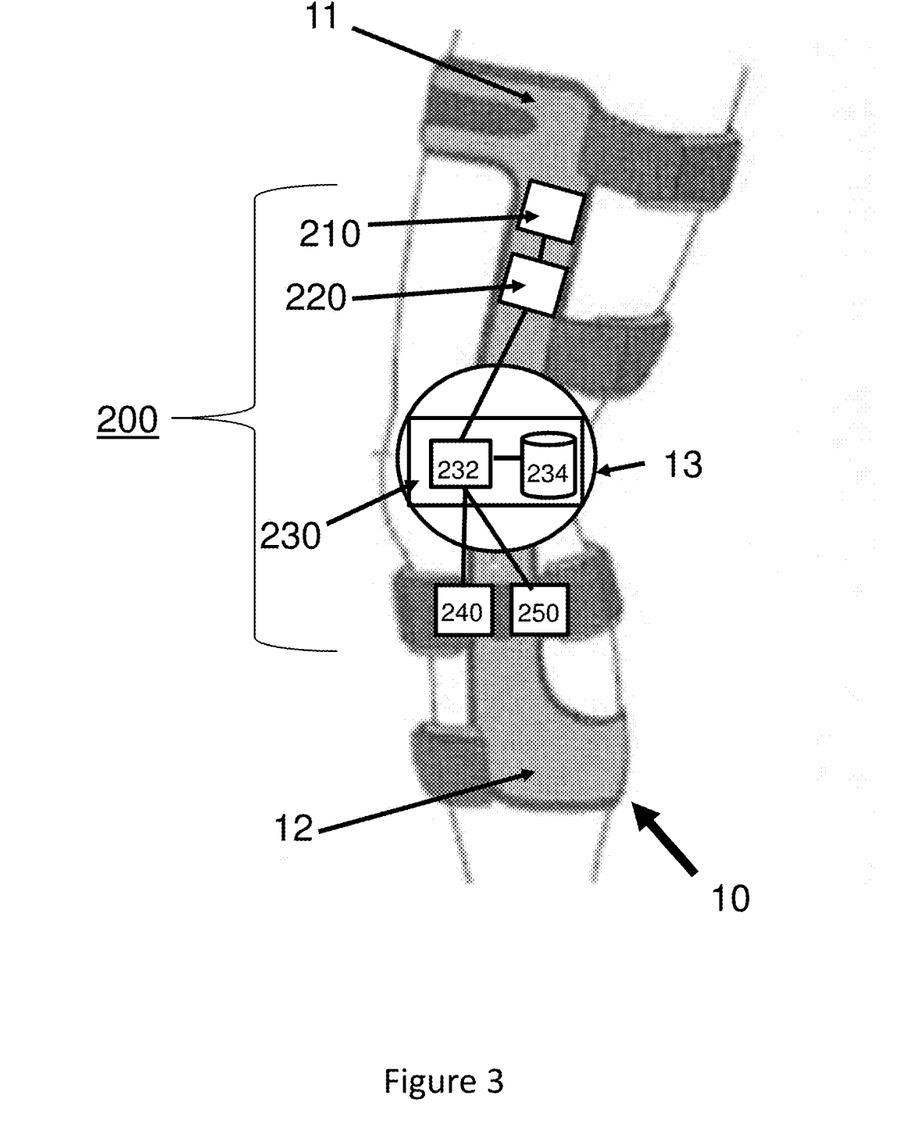
FIG. 3 illustrates the control device 200 implemented on an orthosis 10, according to another exemplary aspect of the claimed invention.

FIG. 3 illustrates the control device 200 implemented on an orthosis 10, according to another exemplary aspect of the claimed invention.

As illustrated in FIG. 3, the control device 200 includes the sensing circuit 210, signal generating circuit 220, and rigidity control mechanism 230. As noted above, the sensing circuit 210 may include an accelerometer, a video capture device, a passive infrared (PR) detection unit having a given field of view, a machine vision/depth camera, a smartphone-based real-time falling detection system.

Although FIG. 3 depicts only one sensing circuit 210 and one signal generating circuit 220 formed on the orthosis 10, the control device 200 may include a plurality of sensing circuits 210 (e.g., a plurality of accelerometers, etc.) and a plurality of signal generating circuits 220 formed at different locations on the orthosis 10, and connected (e.g., by wire) to the rigidity control mechanism 230.

It should also be noted that the sensing circuit 210 and signal generating circuit 220 may be formed separately, or may be formed together as a single unit (e.g., a sensor/signal generator module).

The control device 200 may also include an input device 240 (e.g., keyboard, touch screen) which may be mounted on the orthosis 10 and be used to input data, operating parameters or other data for controlling an operation of the control device 200. Further, the control device 200 may also include a display device 250 (e.g., LED display) which may be mounted on the orthosis 10 and display data (e.g., history data) describing an operation of the control device 200.

As further illustrated in FIG. 3, the orthosis 10 includes an upper frame 11 to be secured above a joint (e.g., in this case, a knee joint), a lower frame 12 to be secured below the joint, and a hinge 13 which connects the upper and lower frames 11, 12, so that the upper and lower frames 11, 12 may be adjustably fixed in relation to each other.

As further illustrated in FIG. 3, the rigidity control mechanism 230 includes a rigidity control circuit 232 which receives the sensing signal from the signal generating circuit 220, and a fluid container 234 which contains a rigidity control fluid such as an electrorheological (ER) fluid or a magnetorheological (MR) fluid. In response to the sensing signal, the rigidity control circuit 232 generates a control signal, which is applied to the rigidity control fluid in the fluid container 234, to cause the viscosity of the rigidity control fluid to change viscosity (e.g., increase a viscosity of the rigidity control fluid or decrease a viscosity of the rigidity control fluid).

The control signal generated by the rigidity control circuit 232 may be, for example, a control signal for generating an electric field (where the rigidity control fluid is an electrorheological (ER) fluid), or a control signal for generating a magnetic field (where the rigidity control fluid is a magnetorheological (MR) fluid). The generated electric field or magnetic field is applied to electrodes on the fluid container 234 and, applied to the rigidity control fluid via the electrodes.

The rigidity of the orthosis 10 depends on the viscosity of the rigidity control fluid. Generally, the greater the viscosity of the rigidity control fluid, the greater the rigidity of the orthosis 10. However, it is possible that the orthosis 10 could be inversely configured such that the greater the viscosity of the rigidity control fluid, the less the rigidity of the orthosis.

Thus, a change of viscosity in the rigidity control fluid causes a change in the rigidity of the orthosis 10. In FIG. 3, the fluid container 234 is connected to the hinge 13 and, therefore, a change of viscosity in the rigidity control fluid causes a change in the rigidity of the hinge 13. For example, the greater the viscosity of the rigidity control fluid, the greater the rigidity of the hinge 13. That is, the greater the viscosity of the rigidity control fluid, the more force that must be applied to the upper frame 11 and/or lower frame 12 in order to change the angle about hinge 13 which is formed by the upper and lower frames 11, 12.

Further, the control device 200 may be able to vary the rate of change in the viscosity of the rigidity control fluid. Thus, for example, the control device 200 may gradually ramp up (or ramp down) the electric/magnetic field in order to gradually change the viscosity of the rigidity control fluid and thereby gradually change the rigidity of the orthosis 10. Alternatively, the control device 200 may near instantly increase (or decrease) the electric/magnetic field in order to near instantly change the viscosity of the rigidity control fluid and thereby gradually change the rigidity of the orthosis 10.

Figure 4:
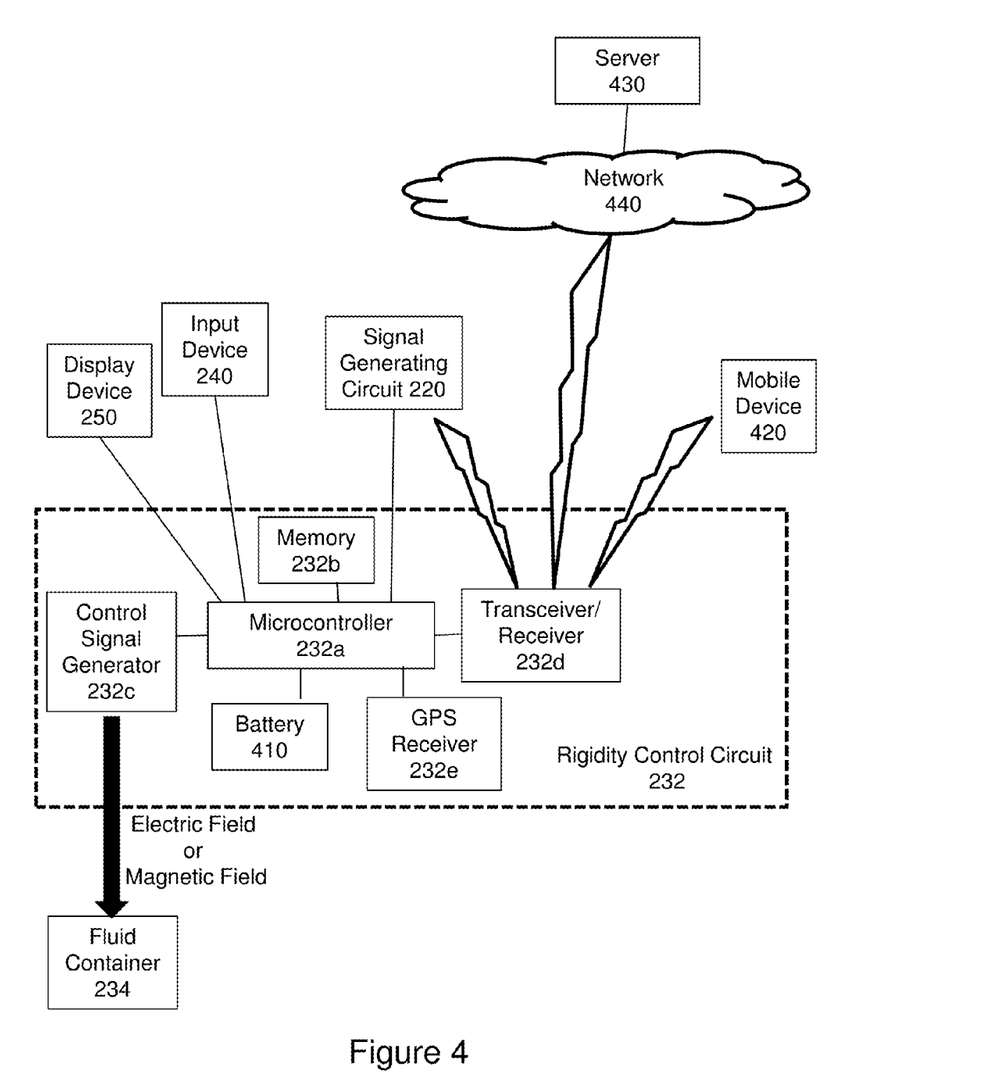
FIG. 4 illustrates the rigidity control circuit 232 according to another exemplary aspect of the present invention.

It should be noted that although FIG. 3 illustrates an orthosis 10 including a hinge 13, the present invention may also be implemented in an orthosis 10 without a hinge. For example, the present invention may be implemented in a flexible or semi-rigid orthosis. Thus, for example, the present invention may be used to transform a flexible or semi-rigid orthosis into a fully rigid orthosis, in order to better protect a broken bone (e.g., if a falling motion is sensed). FIG. 4 illustrates the rigidity control circuit 232 according to another exemplary aspect of the present invention.

As illustrated in FIG. 4, the rigidity control circuit 232 may include a microcontroller 232a for controlling an operation of the control device 200. The rigidity control circuit 232 may be powered by a battery 410, which is connected to the rigidity control circuit 232.

The rigidity control circuit 232 may also include a memory device 232b (e.g., random access memory (RAM)), which is accessible by the microcontroller 232a and stores operating parameters and programming algorithms for operating the control device 200. Thus, the microcontroller 232a may access the memory device 232b to control an operation of the control device 200. In particular, the memory device 232b may store control software, which is executed by the microcontroller 232a to perform a method of controlling a rigidity of the orthosis 10 (e.g., controlling a rigidity of the hinge 213).

In some sense, the control software can be viewed as a personal productivity application because the orthosis 10 may allow the infirm or physically-challenged to experience an increased productivity, increased mobility, and independent living simply because the consequences of falling are mitigated. If the orthosis 10 does detect an actual fall, the control device 200 may transmit appropriate signals and alarms to trained personnel.

The memory device 232b may also store a user profile to allow the control device 200 to be personalized base on the characteristics of the subject wearing the orthosis 10. The user profile may include information such as various information including the subject's cognitive state, mental health state (e.g. whether the subject has Alzheimer's Disease, autism, etc.), physical health state (whether the subject has a physical disability, Parkinson's Disease, etc.). The user profile may also include, for example, the subject's motor-control characteristics, etc.

The memory device 232b may also store falling detection software, which is executed by the microcontroller 232a, as an implementation of the sensing circuit 210.

The microcontroller 232a may also be connected to the input device 240 for controlling an input of data to the memory device 232b by the input device 240. The microcontroller 232a may also be connected to the display device 250 and may generate display data for display on the display device 250.

The rigidity control circuit 232 may also include a control signal generator 232c for generating a control signal (e.g., electrical field or magnetic field) to be applied to the fluid container 234, under the control of the microcontroller 232a.

The rigidity control circuit 232 may also include a wireless transceiver/receiver 232d for wirelessly (or by wire) communicating with devices which are not connected by wire to the rigidity control circuit 232. The transceiver/receiver 232d may transmit and receive wireless signals such as a Wi-Fi signal and a Bluetooth signal.

For example, the transceiver/receiver 232d may be used to wirelessly connect the rigidity control circuit 232 to a mobile device 420 (e.g., mobile phone) or server 430 (e.g., via a network 440) which may include an software application for remotely inputting data and other parameters to the rigidity control circuit 232, which may be stored (by the microcontroller 232a) in the memory device 232b). Thus, for example, the subject which is wearing the orthosis 10 or a person or other entity (e.g., hospital, retirement home, rehabilitation facility) which is in charge of the subject, can use the mobile device 420 or server 430 to remotely adjust the settings of the rigidity control circuit 232 (e.g., update the software stored in the memory device 232b).

The transceiver/receiver 232d may also be used to wirelessly connect the rigidity control circuit 232 to the signal generating circuit 220, so that the sensing signal can be wirelessly transmitted to the rigidity control circuit 232. Thus, for example, in the case where the signal generating circuit 220 is located remotely from the orthosis 10 (e.g., mounted on a wall or on a desktop), the rigidity control circuit 232 may wirelessly receive the sensing signal from the signal generating circuit 220 via the transceiver/receiver 232d.

These features may also allow, for example, a caregiver which is caring for the subject wearing the orthosis 10 to conveniently monitor an operation of the control device 200. For example, microcontroller 232a may cause data such as history data (e.g., rigidity control data which documents the rigidity of the orthosis 10 over the past 30 days, over the past 6 months, etc.) to be communicated (e.g., periodically communicated) to the server 430 and stored on the server 430.

The rigidity control circuit 232 may also include a Global Positioning System (GPS) receiver 232e, which may monitor a location of the orthosis 10, generate location data which describes a location of the orthosis, and transmit the location data to the microcontroller 232a. In this case, the microcontroller 232a may control an operation of the control device 200 based on the location data generated by the GPS receiver 232e. In addition, when the sensing circuit 210 sensing the falling motion, the control device 200 may wirelessly notify medical or emergency personnel (e.g., police, fire, hospital, etc.) for medical assistance through a General Packet Radio Service (GPRS) and the Global Position System (GPS).

For example, memory device 232b may identify a particular location as a "high fall risk area", by associating location data with an event such as a previous fall by the subject. In this case, when the microcontroller 232e detects based on the location data from the GPS receiver 232e that the orthosis 10 is located in a "high fall risk area", the microcontroller 232a may proactively increase a rigidity of the orthosis 10 until the orthosis 10 is no longer located in the "high fall risk area".

Figure 5:
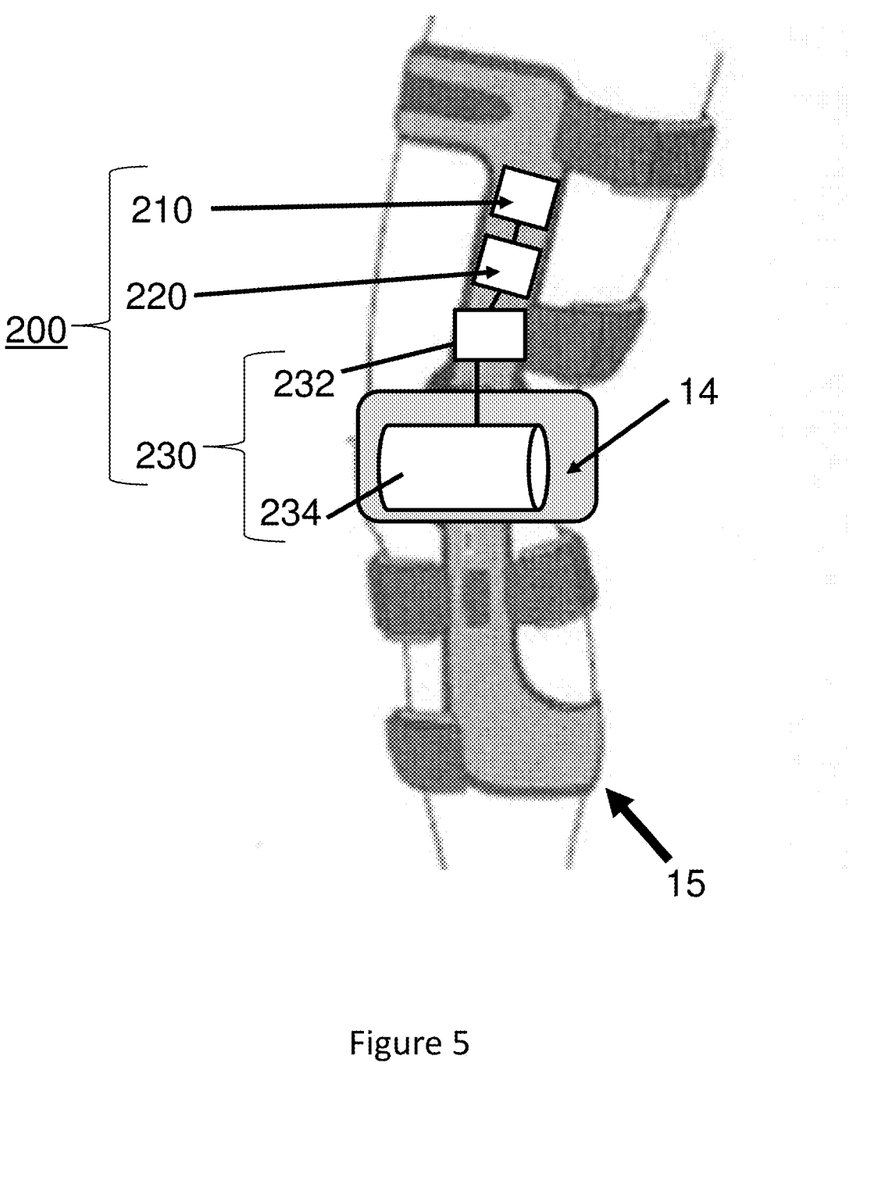
FIG. 5 illustrates the control device 200 implemented on an orthosis 50, according to another exemplary aspect of the claimed invention.

FIG. 5 illustrates the control device 200 implemented on an orthosis 50, according to another exemplary aspect of the claimed invention.

Although the fluid container 234 is illustrated in FIG. 3 as being formed on the hinge 13, the fluid container 234 may be located elsewhere. For example, in the exemplary aspect in FIG. 5, the fluid container 234 is located in a pad 14 of the orthosis 15. In this case, the pad 14 may be in contact with the subject (e.g., in contact with the skin of the subject's leg) and the fluid container 234 may be formed inside the pad 14 or on a surface of the pad 14.

The fluid container 234 in this case may have a bladder configuration with deformable walls, so that a change in viscosity of the fluid translates into a change in rigidity of the pad 14. Thus, when the sensing circuit 210 senses a falling motion, the rigidity control mechanism 230 may increase the viscosity of the fluid (ER fluid or MR fluid) in the fluid container 234, in order to increase the rigidity of the pad 14.

It should also be noted that the control device 200 may control the rigidity of the orthosis 10, 15 to have a plurality of degrees of rigidity. That is, by the rigidity of the orthosis 10, 15 can be set by the rigidity control mechanism 230 to have 10% rigidity, 20% rigidity and so on up to fully rigid (e.g., 100% rigidity). This may be implemented, for example, by varying an intensity (e.g., power) of the electric/magnetic field applied to the fluid container 234. This may also be implemented by having a plurality of fluid containers 234 of varying sizes and/or at varying locations on the orthosis 10, 15, so that, for example, where less rigidity is desired, the rigidity control mechanism 230 may apply the electric/magnetic field to first fluid container 234, and where greater rigidity is desired, the rigidity control mechanism 230 may apply the electric/magnetic field to a second fluid container 234 which has a size that is greater than a size of the first fluid container 234 (i.e., a volume of rigidity control fluid in the second fluid container 234 is greater than the volume of rigidity control fluid in the first fluid container 234).

Figure 6:
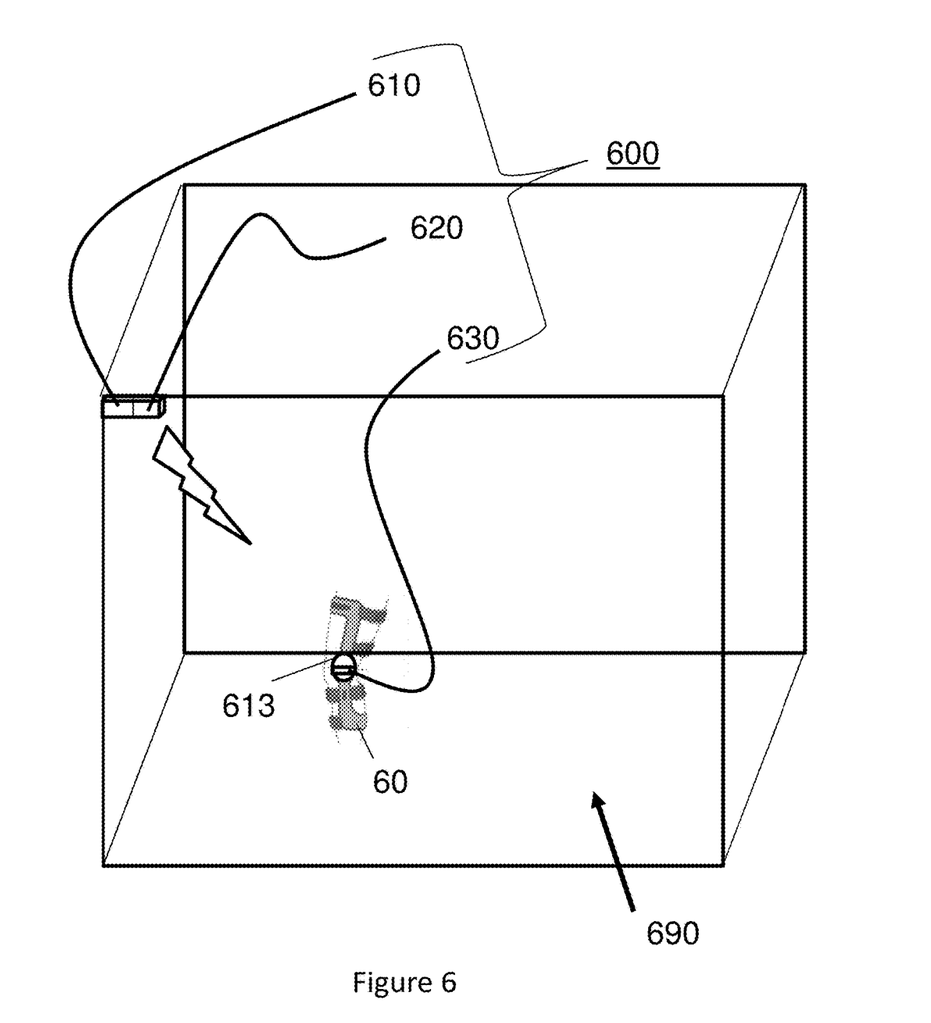
FIG. 6 illustrates a control device 600, according to another exemplary aspect of the claimed invention.

FIG. 6 illustrates a control device 600, according to another exemplary aspect of the claimed invention.

As illustrated in FIG. 6, the control device 600 includes a sensing circuit 610 (e.g., motion sensor) formed on a structure (e.g., a wall of a building) remote from the orthosis 60. The control device 600 also includes a signal generating circuit 610 (e.g., motion sensor) formed on the structure remote from the orthosis 60. For example, the sensing circuit 610 and the signal generating circuit 620 may be formed as a unit as illustrated in FIG. 6. The control device also includes a rigidity control mechanism 630 which is formed on a hinge 613 of the orthosis 60, and which is wirelessly connected to the signal generating circuit 620.

Machine Learning

As noted above the memory device 232b may store data (e.g., user profile) and operating software for controlling the operation of the control device 200. Such data may be input via the input device 240 into the memory device 232b.

An operation of the control device 200 may also be controlled by information (e.g., learning data), which the control device has "learned". That is, the control device 200 may "learn" to predict a future event (e.g., behavior of the subject) based on past events or other input data. Thus, for example, the control device 200 may infer that the subject will fall based on a monitoring by the control device 200 of past falls, or near-falls by the subject.

The control device 200 may "learn" information by utilizing, for example, machine learning models such as support vector machines (SVMs), Neural Networks, AdaBoost classifiers, and other machine learning models. These models (e.g., learning data; data used as input to the learning models and data generated as output by the learning models) may be stored, for example, in the memory device 232b and accessed by the microcontroller 232a, so that the microcontroller 232a can control an operation of the control device 200 based on data generated by the learning models.

In particular, the control device 200 may infer or estimate a confidence level C of an impending fall (e.g., a falling motion) by the subject in real-time, and if the level of C is above a threshold value, the control device 200 may proactively change a rigidity of the orthosis 10 (e.g., change a viscosity of the rigidity control fluid). The threshold value may be stored, for example, in the memory device 232b, and may be set by the subject, the subject's caregiver, and/or the threshold value may be learned and involve machine learning. Further, the cognitive state of the subject (drowsiness, drunk, etc.) and other conditions (e.g., whether the subject has a mental health or physical health issue such as Alzheimer's or Parkinson's Disease) can be considered to properly set the threshold and adjust the rigidity of the orthosis 10.

Any machine learning used to optimize the characteristics of the control device 200 or the orthosis 10, or optimize the response properties of the control device 200 may be performed for a subject (e.g., an individual) or a group of subjects.

It should be noted that in the case where the control device 200 is controlling the rigidity of the orthosis (e.g., preempting a fall of the subject) based on a predicted or inferred "falling motion" (i.e., not based on an output of a sensor such as an accelerometer), the microcontroller 232a and memory device 232b may be considered to constitute the "sensing circuit" and the "signal generating circuit".

The control device 200 may also control the rigidity of orthosis based in part on the output of a sensor such as an accelerometer, and based in part on a predicted or inferred "falling motion". In this case, the sensor, microcontroller 232a and memory device 232b may be considered to constitute the "sensing circuit", and the microcontroller 232a and memory device 232b may be considered to constitute the "signal generating circuit".

Fusing the Output of Multiple Machine Learning Models

Figure 7:
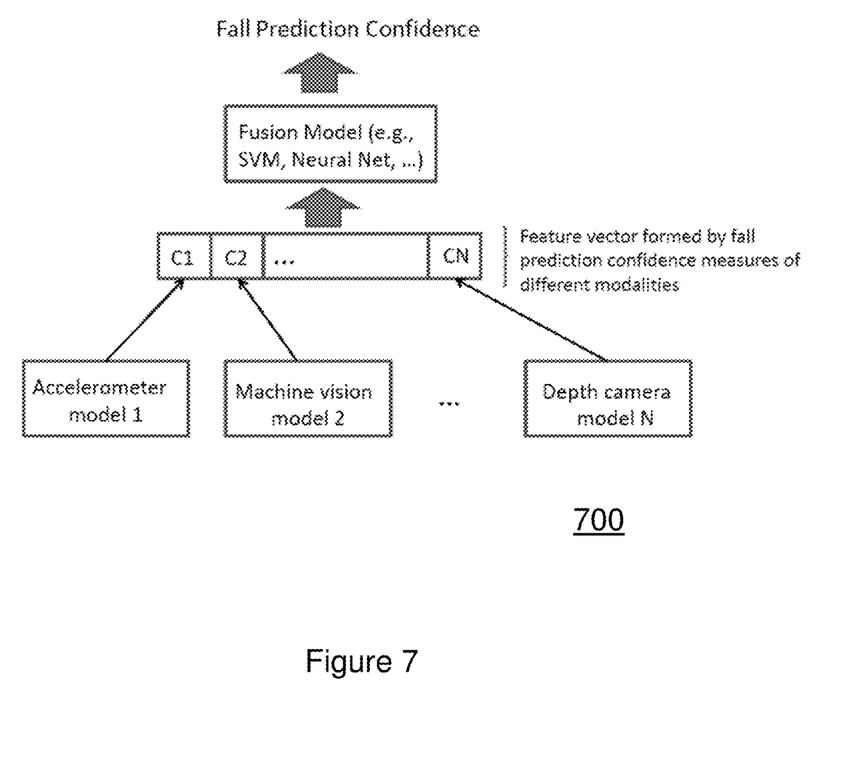
FIG. 7 illustrates a flow chart 700 illustrating a fusing of output of multiple machine learning models, according to an exemplary aspect of the present invention.

FIG. 7 illustrates a flow chart 700 illustrating a fusing of output of multiple machine learning models, according to an exemplary aspect of the present invention.

That is, in an exemplary aspect of the present invention, the confidence of inferring (e.g., estimating, determining, etc.) an impending fall of the subject can be estimated by "fusing" an output of multiple machine learning models trained on different modalities. In this case, the multiple machine learning models (e.g., learning data; data used as input to the learning models and data generated as output by the learning models) may be stored, for example, in the memory device 232b and accessed by the microcontroller 232a, so that the microcontroller 232a can control an operation of the control device 200 based on data generated by the multiple machine learning models.

For example, as illustrated in FIG. 7, a machine learning model 1 may produce fall detection confidence C1 based on an accelerometer (e.g. a first sensing circuit 210), and another machine learning model 2 may produce confidence C2 based on machine vision (e.g., a second sensing circuit 210), and another machine learning model N may produce confidence CN based on a depth camera (e.g., a third sensing circuit 210). The confidences C1, C2, . . . CN produced by these classifiers (e.g., a feature vector formed by fall prediction confidence measures of different modalities) can serve as input features for training a Fusion Model (e.g., a new machine learning model) that outputs the Final Prediction Confidence of an impending fall. The microcontroller 232a may then control an operation of the control device 200 based on the Final Prediction Confidence, which may be stored, for example, in the memory device 232b.

Further, the memory device 232b may store falling detection software that may be used for judging whether the abnormal behavior of falling occurs. In this case, a measured human body posture signal may be generated by the sensing circuit 210 and filtered by the falling detection software. The microcontroller 232a may execute the falling detection software to extract multiple characteristic quantities. Further, data acquired in real time can be input into the falling detection software for detection.

In addition, training of multiple SVM parameters and the weighting coefficient of each SVM may be performed to form an SVM integrated classifier, which may be used by the microcontroller 232a to predict a fall by the subject, and control (e.g., increase) a rigidity of the orthosis 10, 15 in order to preempt the fall by the subject.

Thus, according to one or more sensing circuits 210 (e.g., wearable human body falling detection devices), a classifier can be used for predicting a fall by the subject wearing the orthosis 10, 30, and providing help to the subject, such as when an emergency occurs to an aged human subject.

Controlling Rigidity Based on Location

The control device 200 may also control a rigidity of the orthosis 10, 15 (e.g., perform cognitive-orthosis viscosity change) based on a location of the orthosis 10, 15 (e.g., based on a likely location of a potential fall). For example, the rigidity may be controlled (e.g., the viscosity of the rigidity control fluid may be increased) within a specific radius (or specific surrounding area) of the current location of the subject.

The location of orthosis 10, 15 (i.e., a location of a subject wearing the orthosis 10, 15) can be detected by a location-sensing device on the subject or on the orthosis 10, 15. The orthosis 10, 15 can detect the location (e.g., current location of the subject) using, for example, presser/weight sensors, which are commonly used for the vehicle's "occupant sensor" for detecting the existence of passengers in the car to turn on and off the air bag automatically.

The orthosis 10, 15 can store in the memory device 232b location characteristic information, which indicates whether a particular location is a "high risk" location. Alternatively, the orthosis 10, 15 can communicate (e.g., via the wireless transceiver/receiver 232d) with an external database (e.g., server 430 in FIG. 4) to identify a location of high falling frequency, and determine whether a location has some properties that lead to a high probability of fall, and to determine whether there would be serious consequences if the subject wearing the orthosis 10, 15 would fall at the location.

For example, a subject might suffer a broken bone or other serious injury or even death when falling down a flight of stairs. The control device 200 may forecast of a fall down the flight of stairs, by the mobility prediction based on information gathered by a fall-detection system or a wearable human body falling-detection device. Thus, the control device 200 may control a rigidity of the orthosis 10, 15 (e.g., change the viscosity of the rigidity control fluid proactively) if the control device 200 determines that the subject is in a location with a high fall risk, and or if the control device 200 determines that the subject may suffer severe consequences (e.g., serious injury) in the subject did fall at that location.

The control device 200 may also be configured to predict whether the subject is moving into a location with a high fall risk, and preemptively control the rigidity of the orthosis 10, 15 before the subject enters the location. Thus, for example, the control device 200 may control the rigidity of the orthosis 10, 15 so that the subject cannot move (e.g., gradually lock the hinge 13 on the orthosis 10), to prevent the subject from entering the location with a high fall risk.

Off-the-Shelf Computer Vision-based Classifiers

In another exemplary aspect of the present invention, the sensing circuit 210 may include one or more visual sensors which may be mounted on the orthosis 10, 15 or worn by the subject. The control device 200 may store (e.g., in the memory device 232b) off-the-shelf computer vision-based classifiers (e.g., deep learning systems) can be used to classify visual content into classes such as "stairs", "rough terrain", etc. for fall forecasting based on the output of the one or more visual sensors.

Magnetorheological Dampers and Other Rigidity Control Mechanisms

Although the discussion above has focused on the use of rigidity control fluids (e.g., ER fluids and MR fluids) in the rigidity control mechanism, this approach represents just one possible embodiment.

Figure 8:
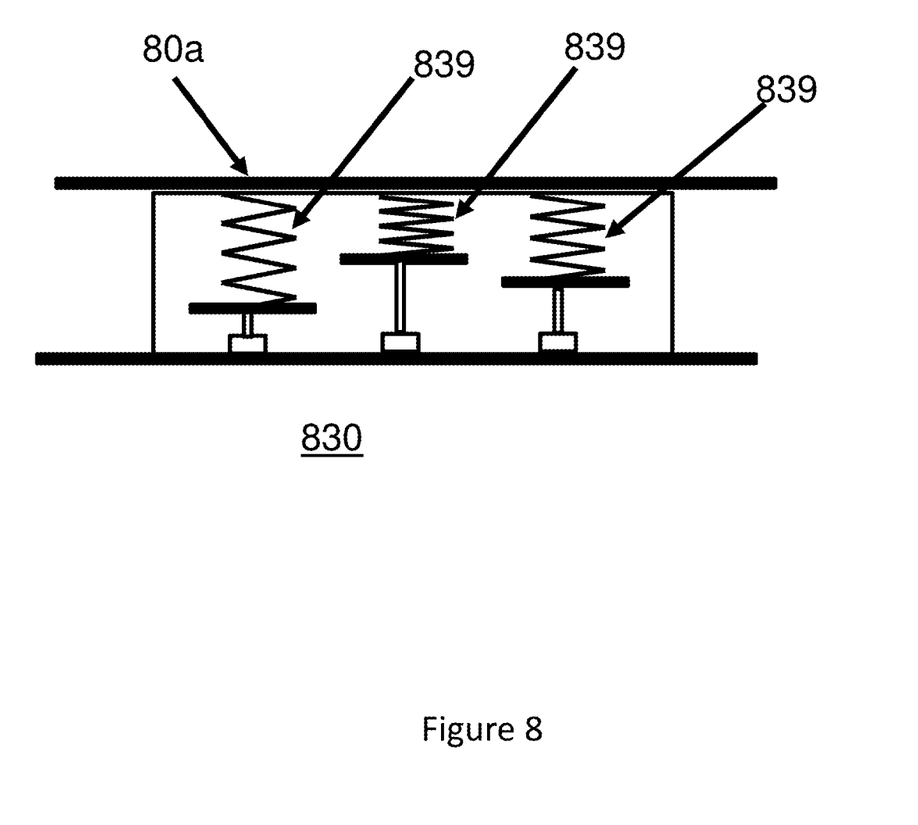
FIG. 8 illustrates a rigidity control mechanism 830, according to another exemplary aspect of the present invention.

FIG. 8 illustrates a rigidity control mechanism 830, according to another exemplary aspect of the present invention.

As illustrated in FIG. 8, the rigidity control mechanism 830 in an exemplary aspect of the present invention, may contemplate deploying a small region of the orthosis 80 with a controlled hardness distribution on a surface 80a of the orthosis 80, using one or more springs 839 with electrically-controlled spring tensions. In this case, the rigidity control circuit 232 may control a rigidity of orthosis 80 by applying a voltage to the springs 839 in order to increase or decrease a tension of the springs, and thereby increase or decrease a rigidity of the orthosis 80.

Another exemplary aspect of the present invention may contemplate small regions of the orthosis with a controllable hardness embodied through the use of the pressure of air fed into small air cells near the surface of the orthosis.

Figure 9:
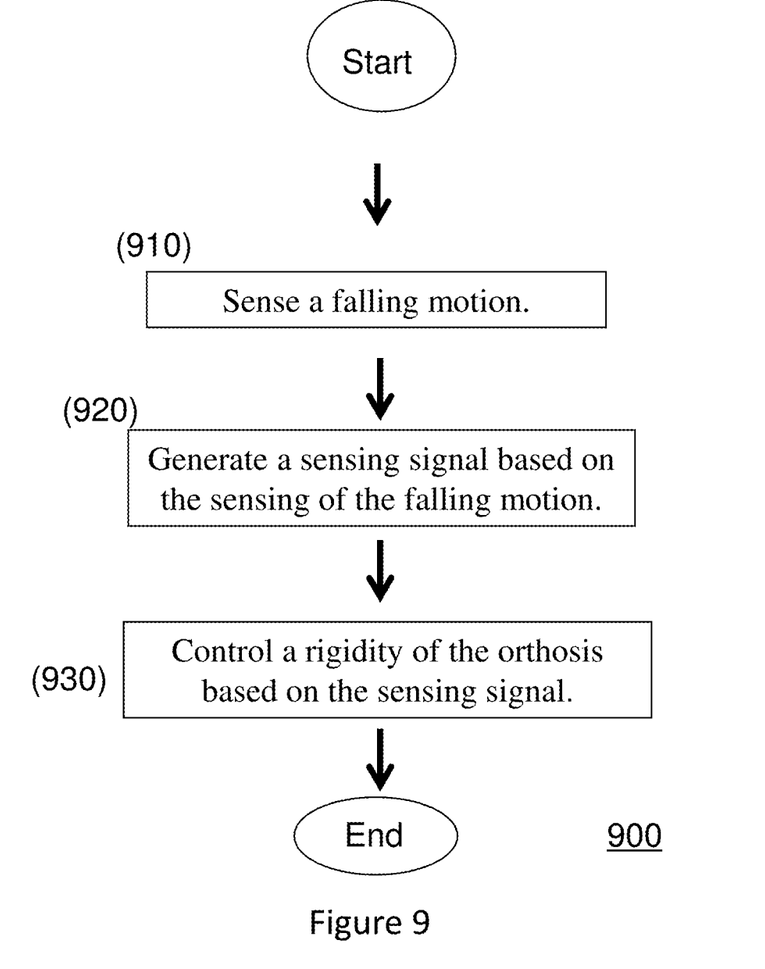
FIG. 9 illustrates a method 900 of controlling a rigidity of an orthosis, according to an exemplary aspect of the present invention.

Referring again to the drawings, FIG. 9 illustrates a method 900 of controlling a rigidity of an orthosis, according to an exemplary aspect of the present invention.

As illustrated in FIG. 9, the method 900 includes sensing (910) a falling motion, generating (920) a sensing signal based on the sensing of the falling motion, and controlling (930) a rigidity of the orthosis based on the sensing signal.

Referring to FIGS. 2-9, another aspect of the present invention is directed to a computer program product which may include, for example, a computer readable storage medium (e.g., memory device 232*b*) (hereinafter, the "storage medium") that may store computer readable program instructions (hereinafter, the "computer program" or "instructions") for performing the features and functions of the control device 200, 600 and performing the method 800. That is, the storage medium may store the instructions thereon for causing a processing device (e.g., computer, instruction execution device, computing device, computer processor, central processing unit (CPU), microprocessor, etc.) to perform a feature or function of the present invention.

The storage medium can be a tangible device that can retain and store the instructions for execution by the processing device. The storage medium may be, for example, but is not limited to, an electronic storage device, a magnetic storage device, an optical storage device, an electromagnetic storage device, a semiconductor storage device, or any suitable combination of the foregoing.

A non-exhaustive list of more specific examples of the storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing.

The storage medium, as used herein, should not be construed as merely being a "transitory signal" such as a radio wave or other freely propagating electromagnetic wave, an electromagnetic wave propagating through a waveguide or other transmission media (e.g., light pulses passing through a fiber-optic cable), or an electrical signal transmitted through a wire.

The processing device can access the instructions on the storage medium. Alternatively, the processing device can access (e.g., download) the instructions from an external computer or external storage device via a network such as the Internet, a local area network, a wide area network and/or a wireless network.

The network may include, for example, copper transmission cables, optical transmission fibers, wireless transmission, routers, firewalls, switches, gateway computers and/or edge servers. For example, the processing device may include a network adapter card or network interface, which receives the instructions from the network and forwards the instructions to the storage medium within the processing device which stores the instructions.

The instructions for performing the features and functions of the present invention may include, for example, assembler instructions, instruction-set-architecture (ISA) instructions, machine instructions, machine dependent instructions, microcode, firmware instructions, state-setting data, or either source code or object code written in one or more programming languages (or combination of programming languages), including an object oriented programming language such as Java, Smalltalk, C++ or the like, and conventional procedural programming languages, such as the "C" programming language or similar programming languages.

The instructions may execute entirely on the processing device (e.g., a user's computer), partly on the processing device, as a stand-alone software package, partly on the processing device and partly on a remote computer or entirely on the remote computer or a server. For example, the instructions may execute on a remote computer, which is connected to the processing device (e.g., user's computer) through a network such as a local area network (LAN) or a wide area network (WAN), or may execute on an external computer which is connected to the processing device through the Internet using an Internet Service Provider.

The processing device may include, for example, electronic circuitry including, for example, programmable logic circuitry, field-programmable gate arrays (FPGA), or programmable logic arrays (PLA) that may execute the instructions by utilizing state information of the instructions to personalize the electronic circuitry, in order to perform a feature or function of the present invention.

It should be noted that the features and functions of the present invention, which are described above with reference to FIGS. 2-9 may be implemented by the processing device executing the instructions. That is, each block of the flowchart illustrations and/or block diagrams, and combinations of blocks in the flowchart illustrations and/or block diagrams, can be implemented by processing device executing the instructions.

The instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

That is, the instructions may be executed by a processing device to cause a series of operational steps to be performed by the processing device to produce a computer-implemented process, so that the executed instructions implement the features/functions/acts described above with respect to the flowchart and/or block diagram block or blocks of FIGS. 2-9.

Thus, the flowchart and block diagrams in the FIGS. 2-9 illustrate not only a method, system, apparatus or device, but also the architecture, functionality, and operation of the processing device executing the instructions. In this regard, each block in the flowchart or block diagrams may represent a module, segment, or portion of the instructions, which comprises one or more executable instructions for implementing the specified logical function(s). In some alternative implementations, the features or functions in the block may occur out of the order noted in the figures.

For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

With its unique and novel features, the present invention provides a control device for controlling a rigidity of an orthosis (and method of controlling a rigidity of an orthosis), which are more effective and more efficient than conventional devices.

While the invention has been described in terms of one or more embodiments, those skilled in the art will recognize that the invention can be practiced with modification within the spirit and scope of the appended claims. Specifically, one of ordinary skill in the art will understand that the drawings herein are meant to be illustrative, and the design of the inventive method and system is not limited to that disclosed herein but may be modified within the spirit and scope of the present invention.

Further, Applicant's intent is to encompass the equivalents of all claim elements, and no amendment to any claim the present application should be construed as a disclaimer of any interest in or right to an equivalent of any element or feature of the amended claim.

What is claimed is:

1. A control device for controlling a rigidity of an orthosis, comprising:
    a sensing circuit for sensing a falling motion;
    a signal generating circuit which generates a sensing signal based on the sensing of the falling motion; and
    a rigidity control mechanism which increases a rigidity of the orthosis based on:
        history data associated with a subject that is wearing the orthosis, the history data including a cognitive state of the subject and a fall history of the subject; and
        the sensing signal indicating the sensing of the falling motion,
    wherein the rigidity control mechanism comprises a location detecting circuit which detects a location of the orthosis, and controls the rigidity based on:
        a level of risk of falling at the detected location; and
        a severity of consequences of falling at the detected location.

2. The control device of claim 1, further comprising:
    a transmitting circuit which transmits the sensing signal to the rigidity control mechanism.

3. The control device of claim 1, wherein the rigidity control mechanism comprises one of:
    an electrorheological (ER) fluid which changes viscosity in response to the sensing signal; and
    a magnetorheological (MR) fluid which changes viscosity in response to the sensing signal.

4. The control device of claim 1, wherein the orthosis comprises one of a cast, a brace, a splint, and a joint hinge.

5. The control device of claim 1, wherein the orthosis is worn by a subject and the falling motion comprises a falling motion or slipping motion of the subject.

6. The control device of claim 5, wherein the rigidity control mechanism comprises a rigidity control circuit comprising:
    a memory device which stores the history data; and
    a processing device which accesses the history data in the memory device, and generates a control signal for controlling a rigidity of the orthosis based on the history data.

7. The control device of claim 5, wherein the rigidity control mechanism comprises a calculating circuit which calculates a confidence level that the falling motion will occur, and controls a rigidity of the orthosis based on whether a value of the calculated confidence level is greater than a confidence level threshold value.

8. The control device of claim 7, wherein the confidence level comprises a real-time confidence level which is calculated by the calculating circuit in real-time, and the rigidity control mechanism proactively controls the rigidity of the orthosis based on the real-time confidence level.

9. The control device of claim 8, wherein the rigidity control mechanism comprises a learning data generating circuit which generates learning data, and controls a rigidity of the orthosis based on the learning data.

10. The control device of claim 9, wherein the confidence level threshold value is dynamically adjusted based on the learning data.

11. The control device of claim 5, wherein the sensing circuit comprises at least one of an accelerometer, a video, a passive infrared (PIR) detection unit having a given field of view, a machine vision/depth camera, a smartphone-based real-time motion detection system, and a subject-wearable falling detection device.

12. The control device of claim 11, wherein the subject-wearable falling detection device comprises embedded-type multi-sensor hardware and falling detection software.

13. The control device of claim 9, wherein the learning data comprises at least one of:
    data based on fusing an output of multiple machine learning models trained on different modalities; and
    data from off-the-shelf computer vision-based classifiers.

14. The control device of claim 5, wherein the rigidity control mechanism comprises a magnetorheological damper.

15. A method of controlling a rigidity of an orthosis, the method comprising:
    sensing a falling motion;
    generating a sensing signal based on the sensing of the falling motion;
    detecting a location of the orthosis and controlling a rigidity of the orthosis based on:
        a level of risk of falling at the detected location; and
        a severity of consequences of falling at the detected location; and
    increasing a rigidity of the orthosis based on:
        history data associated with a subject that is wearing the orthosis, the history data including of a cognitive state of the subject and a fall history of the subject; and
        the sensing signal indicating the sensing of the falling motion.

16. A programmable storage medium tangibly embodying a program of machine-readable instructions executable by a digital processing apparatus to perform a method of controlling a rigidity of an orthosis, the method comprising:
    sensing a falling motion;
    generating a sensing signal based on the sensing of the falling motion;
    detecting a location of the orthosis and controlling a rigidity of the orthosis based on:
        a level of risk of falling at the detected location; and
        a severity of consequences of falling at the detected location; and
    increasing a rigidity of the orthosis based on:
        history data associated with a subject that is wearing the orthosis, the history data including a cognitive state of the subject and a fall history of the subject; and
        the sensing signal indicating the sensing of the falling motion.

17. The control device of claim 1, wherein the rigidity control mechanism controls the rigidity to have a first value if the location detecting circuit detects that the orthosis is located in a first location having a first fall risk, and to have a second value different from the first value if the location detecting circuit detects that the orthosis is located in a second location having a second fall risk which is different from the first fall risk, and wherein the second fall risk at the second location is greater than the first fall risk at the first location, and the second value of the rigidity is greater than the first value of the rigidity.

18. The control device of claim 17, wherein the rigidity control mechanism comprises a memory device which stores the history data, wherein the history data comprises data pertaining to a past sensing of a falling motion, and wherein the memory device stores data identifying the second location as a high fall risk area by associating the second location with the data pertaining to a past sensing of a falling motion.

\* \* \* \* \*